US010545095B1

(12) United States Patent
Spicola et al.

(10) Patent No.: US 10,545,095 B1
(45) Date of Patent: Jan. 28, 2020

(54) HIDE GRADING SYSTEM AND METHODS (71) Applicants: Joseph A. Spicola, Tampa, FL (US); David Fairbanks, St. Petersburgh, FL (US); Bryan C. Parent, Valrico, FL (US)

(72) Inventors: Joseph A. Spicola, Tampa, FL (US); David Fairbanks, St. Petersburgh, FL (US); Bryan C. Parent, Valrico, FL (US)

( * ) Notice: Subject to any disclaimer, the term of this patent is extended or adjusted under 35 U.S.C. 154(b) by 0 days.

(21) Appl. No.: 16/223,412

(22) Filed: Dec. 18, 2018

(51) Int. Cl.
*G01N 21/88* (2006.01)
*G01N 33/44* (2006.01)
(Continued)

(52) U.S. Cl.
CPC ..... *G01N 21/8806* (2013.01); *G01N 21/8803* (2013.01); *G01N 21/9515* (2013.01);
(Continued)

(58) Field of Classification Search
CPC .......... G01N 2800/24; G01N 2800/60; G01N 2500/20; G01N 33/483; G01N 33/573; G01N 33/57492; G01N 33/6893; G01N 15/06; G01N 15/0656; G01N 15/1404; G01N 1/10; G01N 2015/003; G01N 2015/0053; G01N 2015/0662; G01N 2015/0687; G01N 2015/0693; G01N 2021/3595; G01N 2021/6417; G01N 2021/8411; G01N 2035/00881; G01N 21/31; G01N 21/3577; G01N 21/64; G01N 21/643; G01N 21/65; G01N 21/85; G01N 21/8507; G01N 21/87; G01N 21/8851; G01N 21/94; G01N 21/95; G01N 2201/10; G01N 2333/70596; G01N 2333/765; G01N 2333/79; G01N 2333/936; G01N 2333/96419; G01N 2333/96455; G01N 2500/04; G01N 2800/085;
(Continued)

(56) References Cited

U.S. PATENT DOCUMENTS 1,704,386 A  3/1929  Harding
2,623,291 A  12/1952  Hay et al.
(Continued)

FOREIGN PATENT DOCUMENTS

WO  WO 2008/022248 A2  2/2008
WO  WO 2008/064685 A1  6/2008

*Primary Examiner* — Michael P Stafira (57) ABSTRACT

The invention comprises a method and system for grading and verifying the grading of an animal hide. The animal hide is inspected on a light table to determine the grade of the hide. A tag on the hide is read by a reader to identify the hide. The hide is displayed on a monitor connected to a computer. Touch screen commands are be used for inputting information into the computer database to make a record of the inspection and grading of the hide. A camera connected to the computer is used to photograph the animal hide on the light table and store the data and image in a computer database to make a record of the inspection and provide the ability to verify the condition of the animal hide when it was inspected. The photograph of an animal hide and all information relating to the animal hide is stored in a database to identify the hide and to verify the inspection grade of the animal hide.

17 Claims, 5 Drawing Sheets

(51) Int. Cl.
*G01N 21/95* (2006.01)
*G06K 7/10* (2006.01)
*G06K 7/14* (2006.01)

(52) U.S. Cl.
CPC ....... *G01N 33/447* (2013.01); *G06K 7/10297* (2013.01); *G06K 7/1413* (2013.01)

(58) Field of Classification Search
CPC ......... G01N 2800/162; G01N 2800/52; G01N 33/2858; G01N 33/2876; G01N 33/2888; G01N 33/46; G01N 33/49; G01N 33/50; G01N 33/5005; G01N 33/502; G01N 33/564; G01N 33/574; G01N 33/57407; G01N 33/57423; G01N 33/57434; G01N 33/57484; G01N 33/6827; G01N 33/6854; G01N 33/92; G01N 35/00871; G06K 9/6202; G06K 9/66; G06K 9/00; G06K 9/00026; G06K 9/0014; G06K 9/00335; G06K 9/3233; G06K 9/42; G06K 9/527; G06K 9/6262; G06K 9/6269; G02B 2027/0138; G02B 2027/014; G02B 2027/0141; G02B 27/01; G02B 27/0101; G02B 27/286
See application file for complete search history.

(56) References Cited

U.S. PATENT DOCUMENTS

| | | | |
|---|---|---|---|
| 4,199,255 A | 4/1980 | Wilson et al. | |
| 5,096,553 A | 3/1992 | Ross et al. | |
| 5,220,614 A * | 6/1993 | Crain | G06K 9/00 348/128 |
| 5,838,569 A * | 11/1998 | Gane | B26D 5/00 700/134 |
| 6,157,730 A * | 12/2000 | Roever | G01N 21/89 382/110 |
| 9,951,294 B2 | 4/2018 | Hein et al. | |
| 2010/0058818 A1* | 3/2010 | Houtz | C14B 1/28 69/33 |
| 2013/0176422 A1* | 7/2013 | Campbell | B26D 5/007 348/95 |
| 2013/0177215 A1* | 7/2013 | Campbell | B26F 1/3813 382/111 |
| 2014/0208902 A1* | 7/2014 | Gordon | C14B 5/02 83/13 |
| 2015/0344980 A1 | 12/2015 | Hein et al. | |
| 2017/0243284 A1* | 8/2017 | Rubman | G06Q 30/08 |

\* cited by examiner

HIDE GRADING SYSTEM AND METHODS

CROSS-REFERENCE TO RELATED APPLICATIONS

NS

STATEMENTS REGARDING FEDERALLY SPONSORED RESEARCH OR DEVELOPMENT

NA

REFERENCE TO A MICROFICHE APPENDIX

NA

BACKGROUND OF THE INVENTION

1. Field of the Invention

The invention relates to animal hide grading systems and methods. Presently companies are using a table that has recessed lighting underneath with a clear or plain glass on top. The grader takes a hide and puts it on top of the table. The grader or another person scans the RFID tag and reads it. Another person may verify the RFID tag reading. The grader views the hide and may measure it to grade it. The grade can be Grade 1, 2 or 3 depending on the size and condition of the hide. Another person may grab the hide after it's graded by the grader and then that hide is sorted into grade piles. There are multiple people doing multiple tasks.

One person pulls the hide on the top of the glass table which has a light underneath it that shines through the hide allowing the grader to see it much better for grading as well as how it is made up. Another person identifies and reads the bar code on the hide which is how you differentiate between other hides and know which is which. The person reading off the bar code data either enters the information on a paper form or by typing it into a computer which is then passed on to another individual to be sorted. The skilled person in this is the grader.

You may have two people getting the hide ready for grading and identification plus the grader and another person that takes the graded hides and sorts them. During the grading, a ruler is used to measure the hide which is recorded. The information is typically written down on a clipboard and form or the grader calls off the information to another person who enters it into a computer. This procedure is subject to human errors.

Examples of the human errors that are problems are as follows. Whoever buys the hides go through every hide that they purchased to verify that the hide was graded correctly. It is common for the grader of the buyer to differ from the grader of the seller. The buyer grader may then downgrade a hide from a Grade 1 to a Grade 2 or 3. The buyer grader may be in Milan, Italy and the seller is in the United States. It is difficult to challenge the buyer grader when you cannot objectively view the hide and see the basis for the downgrade. The person buying the hide says they are a lower grade and they will only pay the lower grade price. The grader and seller must be able to prove that they were the correct grade to get paid the full amount. If the seller is in the United States and you sold it to someone who's in Milan, Italy, you have no way to challenge this unless you travel there. Furthermore, when the buyer calls and says that they received a whole bunch of Grade 2's but paid for Grade 1's can be very problematic. The buyer may say that it found 50 of the Grade '1s that are Grade 2's and since the buyer paid for Grade 1's, it reduces the payment accordingly and may quickly add up to hundreds of thousands of dollars. One can disagree that the hides were graded wrongly but cannot effectively challenge from overseas. The seller must trust the overseas buyer or have the grader inspect the hide at the seller's location. This is a common thing that happens when the seller challenges the grades and there's no trackability to I so it is a difficult task to prove that the hides were graded correctly.

It is an object of the invention to speed up the grading process of hides. Another object of the invention is to make the job of the grader easier. Another object of the invention is to reduces errors in grading hides. Another object of the invention is to help train graders to do their job of grading. Another object of the invention is to provide a record of the grading of a hide. Another object of the invention is to provide a system that can be used to verify that the hides have been properly tracked. Another object of the invention is to allow the seller to verify with the buyer that the proper grade was given to the hide. Another object of the invention is to increase the profits of the seller and avoid downgrading of a hide.

2. Description of the Related Art

U.S. Pat. No. 1,704,386 discloses a machine for grading hides and skins of un-even and varying thicknesses. It indicates the average thickness of a hide or skin at a plurality of points along its length.

U.S. Pat. No. 2,623,291 discloses an apparatus for gauging and grading leather by ascertaining the direct percentage of good leather to the total area of leather.

U.S. Pat. No. 4,199,255 discloses an apparatus for grading hides, skins, pelts and the like according to thickness and quality including means, for example a mechanical/electrical transducer, for providing a signal representing the thickness of a selected skin. Manually operated push-buttons provide a signal representing the quality of the skin and means responsive to both these signals for providing a signal representative of a product category for the skin. The product category signal may serve for sorting the skins into batches and preferably controls the application of an area signal for each selected skin in a category to summation means therefor enable control and/or display of total batch area. The skins may pass through the apparatus on an endless conveyor above which are disposed photoelectric scanning means to detect instantaneously the width of each passing skin to provide the area signal and a thickness transducer to bear against the skin to provide the thickness signal.

U.S. Pat. No. 5,096,553 discloses a method of treating raw animal hides and skins prior to tanning, wherein the hides and skins are initially washed, trimmed, fleshed and demanured, including the steps of dipping the hides and skins in a dilute antiseptic solution for a predetermined amount of time, removing excess moisture from the hides and skins following dipping, and irradiating the hides and skins with substantially monodirectional electron beams to expose each hide and skin to a dose adjustable within the range of 0.75 to 4.0 Mrads at a dose rate adjustable within the range of 105 to 107 rads/sec.

U.S. Pat. No. 9,951,394 discloses a method and system for processing raw animal hides into leather are provided. It comprises a tanning manager that directs the routing of hides to a plurality of tanning drums. This allows the tanning manager to efficiently use the capacity of the plurality of tanning drums and provides improved consistency in the tanning of the hides. Furthermore, one or more embodiments enable the tanning manager to route hides to tanning drums based on various factors, such as hide type, hide weight, and hide size. In addition, one or more embodiments provide the tanning manager with greater control over the processing of hides into leather by customizing the tanning recipes applied to each batch of hides U.S. Patent Application Publication No. US 2013/0177215 A1 discloses a computer program for processing coverings such as leather hides and fabrics are provided. The method for processing coverings can include placing a covering on a work surface and projecting a captured image of the covering by a projector onto the covering. Virtual markings of boundary lines and defects on the covering on the capture image can be registered using the controller. Nesting of templates can be performed on the captured image of the covering with the virtual markings and the nested templates stored as virtual markings with the captured image of the covering. The covering can then be marked, die pressed, or cut along the virtual markings.

U.S. Patent Application Publication No. US 2015/0344980 A1 discloses a method and system for sorting hides are provided. It comprises a tanning control system that enhances the traceability of hides by capturing and utilizing data related to the unloading, tanning, sorting, and packaging of hides. Furthermore, one or more embodiments enable the tanning control system to improve efficiency by sorting hides based, at least in part, on data generated during prior tanning processes. Additionally, one or more embodiments facilitate the tanning control system in customizing the sorting and packaging of hides based, at least in part, on one or more hide characteristics and/or customer specifications.

International Published Application No. WO 2008/022248 A2 discloses a method and system for processing animal hides in a meat processing facility. The system includes a grading station for determining hide grades, a measuring station for determining at least one hide dimension of the animal hide, a hide folding station, a stacking station adapted to deposit hides at a plurality of stacking sites, a conveyor system and a control system.

International Published Application No. WO 2008/064685 A1 discloses an individual identification and transport system for use in the handling of killed furred animals and fur pelts, namely mink and mink pelts on mink farms, pelt processing plants, collection and sorting centers, auction houses, tanneries, and with other processing of pelts from furred animals, which is characterized in that it comprises an electronically readable data media (6) for individual identification data (ID-data) for an actual furred animal, and where the electronically readable data media (6) is integrated in a transport and handling arrangement (2) which is inserted through the nostrils of a relevant furred animal immediately after the furred animal has been killed, said transport and handling arrangement (2) constituting a part of a transport and handling system for transport and handling of furred animals and pelts, and which remains together with the pelt from the time at which it is inserted into the pelt until this is processed into furs. The system uses emptying/filling stations and computer-controlled sorting plants to reduce the amount of manual work for the fur farmer as well as at the auction houses.

BRIEF SUMMARY OF THE INVENTION

The invention comprises a method and apparatus for grading and verifying the grading of an animal hide. An animal hide is placed on a light table to illuminate the hide and allow determination of the grade of the hide. A tag or label on the hide is automatically read to identify the hide. The hide is displayed on a touch screen monitor connected to a computer. The grade of the hide is set by selecting the grade of the hide on a touch screen monitor. The grader can select the top and lower scutes of the hide on the monitor image of the hide with touch commands on a touch screen monitor to provide a measurement of the hide between scutes. A ruler is displayed on the animal hide image so that its dimensions are shown on the image. The animal hide on the light table is photographed with a camera and the data and image are stored in a computer database to make a record of the inspection. The stored photograph of an animal hide and all information relating to the animal hide in a database is used to identify the hide and to provide verification of the inspection grade of the animal hide.

DETAILED DESCRIPTION OF THE INVENTION

Figure 1:
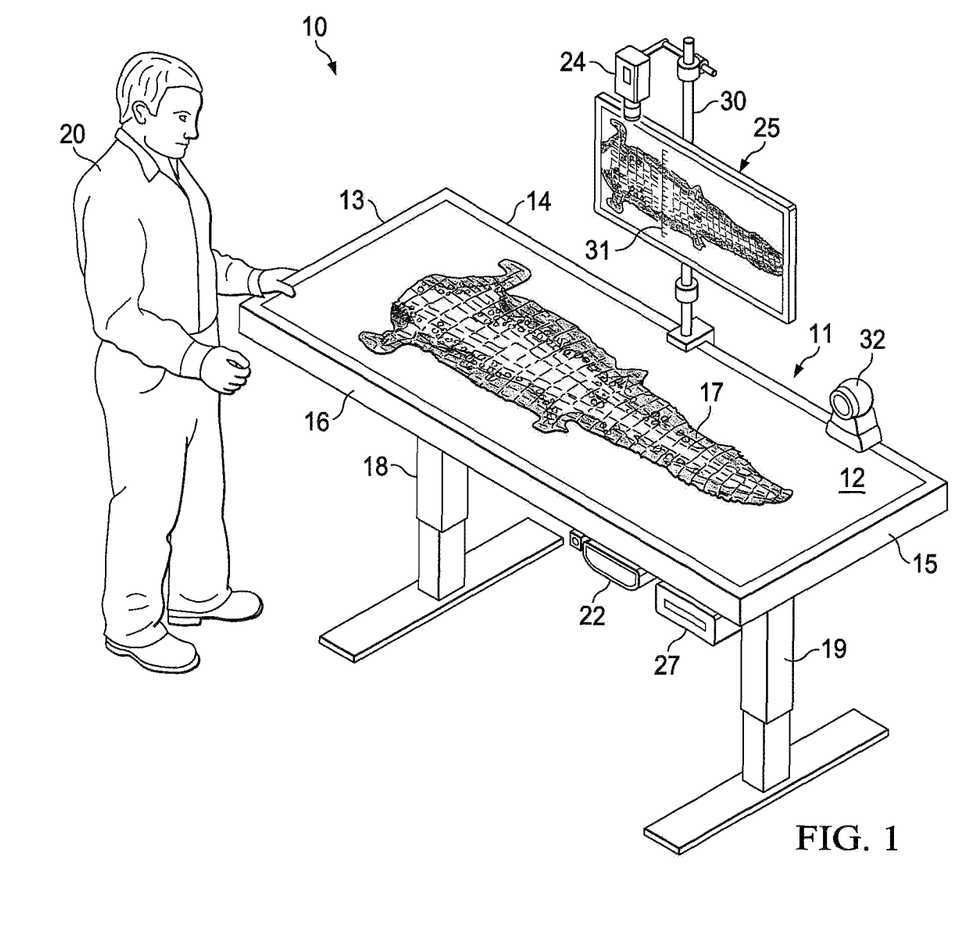
FIG. 1 is a perspective view of the grading system in use.

The preferred embodiment comprises a grading system 10 and a light table 11. Referring to FIG. 1, the light table 11 has a translucent high-density poly propylene top 12 that may be about one-half inch in thickness with a left side 13, back side 14, right side 15 and front side 16.

A led light source comprising a bank of multiple lights in spaced relationship is provided under the translucent top 12 to uniformly and brightly illuminate the top 12 so that it will illuminate a hide or hide 17 that is placed on the top for grading. The hide is slightly translucent so the light shining on the underneath of the hide will illuminate the hide and show flaws in the hide such as holes or gaps. The light will allow a grader 20 to see imperfections in the hide such as holes or gaps which would automatically show up in the record inspection. The table 11 includes adjustable height legs 18 and 19 to allow positioning the height of top 12 relative to a grader 20. Table controls 22 control the operation of the table 11.

Figure 2:
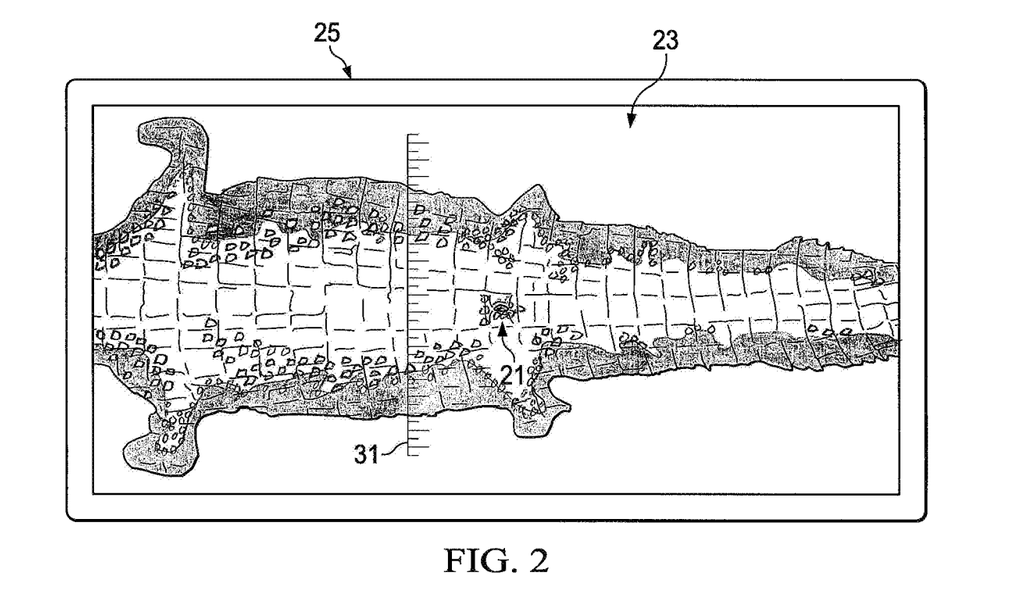
FIG. 2 is a view of an image of an animal hide on a viewing monitor with superimposed measuring rules on the image.
Figure 3:
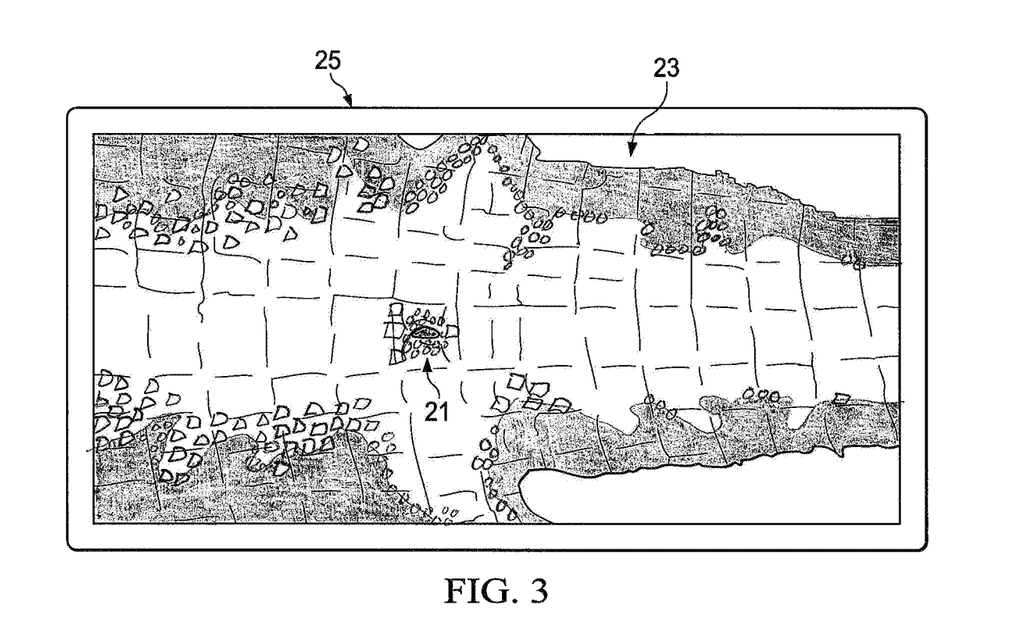
FIG. 3 is an enlarged portion of the animal hide image on the viewing monitor.

An adjustable monitor support 30 is provided to support a viewing monitor 25. The touch screen monitor 25 is attached to the monitor and camera support 30 and can be adjusted on the monitor support 30. The touch screen monitor displays an image 23 of the hide 17 as shown in FIGS. 2-3. A camera 24 is provided to view a hide 17 laying on the top surface of the top 12. The camera 24 may be a high-resolution web camera 24 to take a high-resolution photograph of a hide 17 on the table 11. An example of a current high-resolution web camera is a 4K web camera. The camera 24 can be mounted on its own adjustable support or can be mounted on the monitor support. The camera 24 can be adjusted in height on the support 30. A bar code reader 32 is provided on the table to read bar codes on the hide 17 to also identify the hide. A RFID reader 26 is also provided on the table to read an RFID tag on the hide 17 to identify it.

Some states require a barcode reader 32 and barcodes on the hide to identify the source of the hides. A bar code reader 32 is mounted on the side of the light table to read the bar code when the hide is positioned to be read. This reduces the number of people required and reduces errors. The barcode reader 32 is mounted on the right side of the top of the table below the monitor so when you slide the hide across the table you get a ping and you know it's read. Everything is pinged, so when it reads the barcode it's one ping; when it reads the RFID it's another different tone ping. The bar code reader 32 may be an omnidirectional reader, so its spinning all the time looking for something to read. When you lay the hide on the table it might take a second to catch the bar code, read it, and get a ping.

Figure 6:
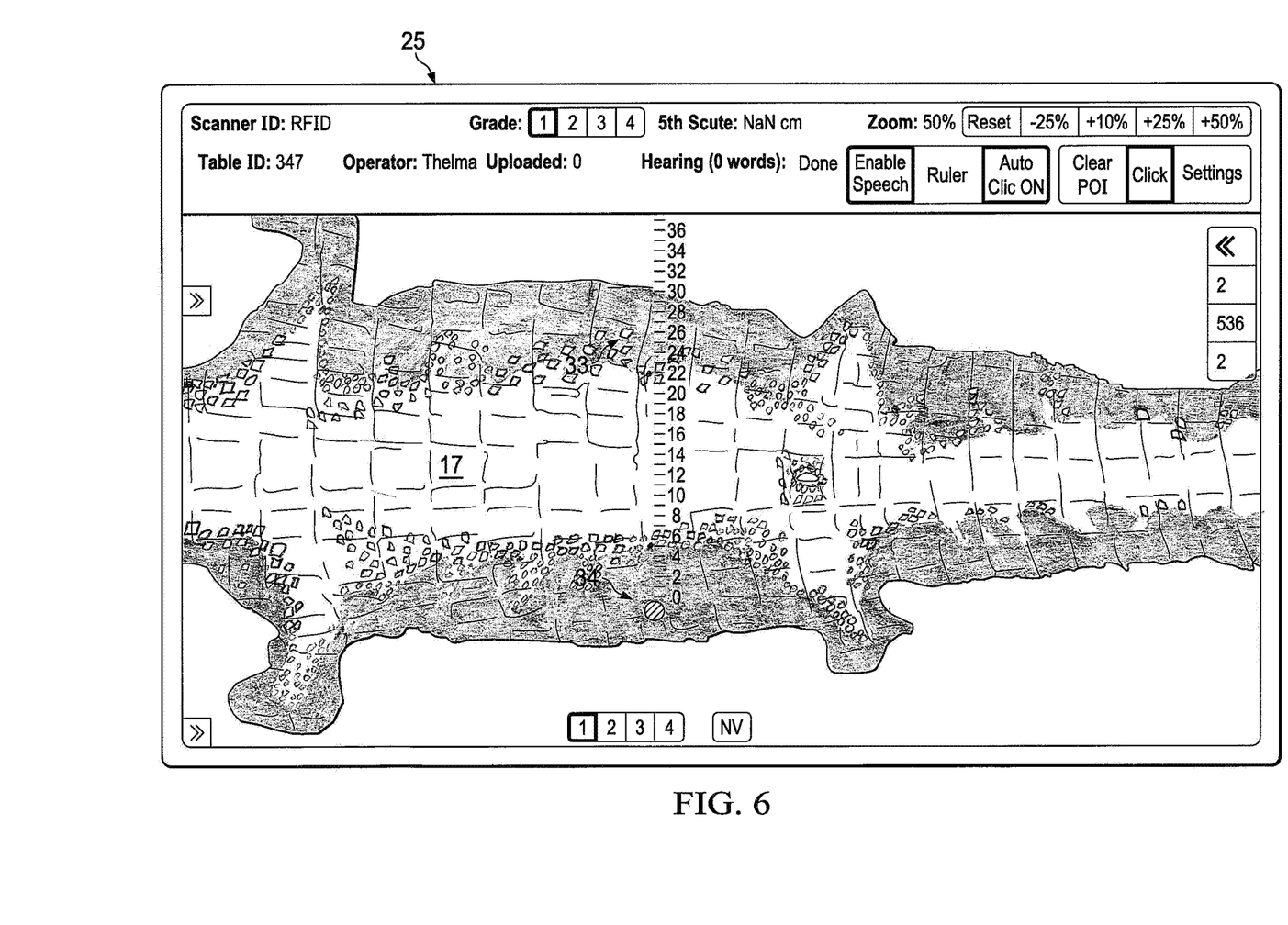
FIG. 6 is a view of the touch screen monitor with a hide displayed on it.

The steps that a hide grading undergoes when you lay it on the light table is as follows. Step 1, you lay the hide on the table. Step 2, the barcode is read by the barcode reader on the table. The RFID is also read if it has an RFID on it. Step 3, the system is defaulted to a Grade 1. Most of the hides that are sent to grading are Grade 1. As shown in FIG. 6, if it's a Grade 2, 3 or 4, on the bottom of the touch screen monitor 25 there are 2, 3 and 4 touch points and you can touch the appropriate block on the touch screen monitor 25 if it is a 2, 3 or 4 to indicate a different grade. You do not have to touch the 1 touch point if the grade is a grade 1 because it automatically reverts to a grade 1 even if you graded the previous hide a grade 2 by touching the 2-touch point.

Figure 5:
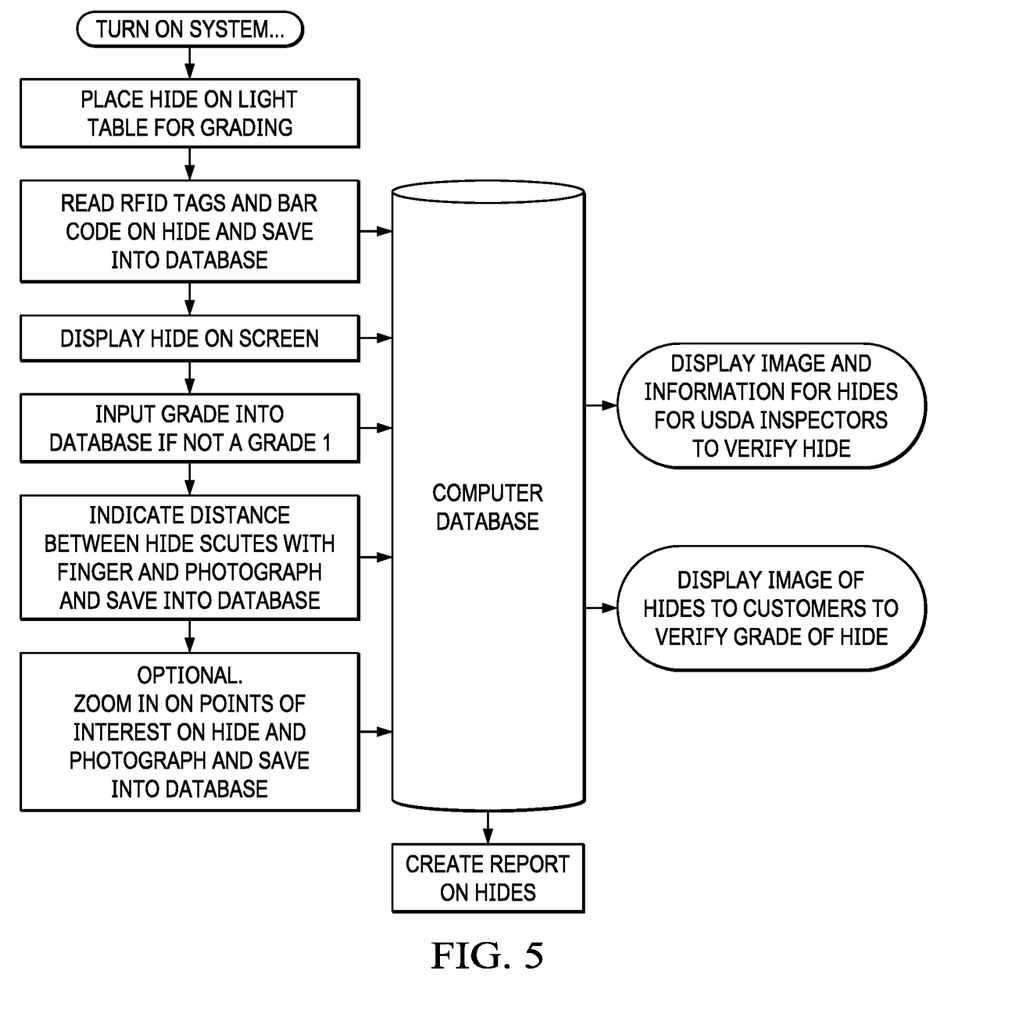
FIG. 5 is a flow chart of the method of the grading system.

Step 4 is measuring from the scutes which are at the top and the bottom of the hide belly. A scute or scutum is a bony external plate or scale overlaid with horn on the skin of alligators. Bony plates inside the alligator skin, called osteoderms or scutes, make the skin very hard to penetrate. When you look at the ridges on the back of an alligator, each little spike is made by a piece of bone in that section of skin. The area between the top first row of scutes and bottom first row of scutes is the part of the hide that is used to make products. The light area between the neck and vent in FIG. 5 is the part of the belly skin that is graded. Holes or cuts in this part of the skin make it difficult or impossible to cut full belly patterns for purses, briefcases or larger leather articles. Enough holes or cuts in the flanks can even make cutting shoe vamps or smaller leather-goods difficult. The one row of scutes along the sides of the alligator are left so the tanner has some extra skin to tack to when the skin is stretched and dried during the tanning process.

Referring to FIG. 6, the grader puts his finger on the top scute 33 as displayed as hide image 23 on the touch screen monitor 25 until a crosshair appears. The crosshair will move with the finger until the finger is released at the desired location on the top scute 33. You put your finger on the lower scute 34 until another crosshair appears and you move the finger until the finger is released on the lower scute 34. This automatically measures width of the hide belly between the top and lower scutes 33 and 34. When it records the measurement between the scutes, which might be a 33 or 38, the camera 24 takes a picture. Once that measurement is made on the hide, a picture is taken, and you may remove the hide, bring on the next hide, and start all over again. This reduces the amount of time required to grade a hide and reduces errors in grading. Also, a record is made of the grading that can be reviewed later to verify the hide grade. If the grade of the hide is later questioned by the buyer of the hides, which is typically overseas, the record can be used to confirm that the grade was correctly made. If an error was made it can be confirmed by looking at the photographic record of the hide during grading. If a hide is damaged during tanning or after it is shipped overseas, this can also be determined. Because fewer errors are made in grading, the seller is less likely to have to take a lower price for a hide because the seller downgrades the grade of the hide. The grade of each hide is verified by the buyer and the seller does not have to be present with the buyer's grader to confirm if the hide was graded correctly The barcode reader 32 is mounted on the right side of the top of the table 12 below the monitor 25 so when you slide it across you get a ping and you know it's read. Everything is pinged, so when it reads the barcode it's one ping; when it reads the RFID it's another different tone ping. The bar code reader 32 may be an omnidirectional reader, so it is spinning all the time looking for something to read. When you lay the hide on the table it might take a second to catch the bar code, read it and get a ping.

The hides are cured before shipping to remove moisture from the skin, so it can be better preserved before tanning. Salt is applied to a hide and the salt is rubbed onto the skin. The salt gets into the creases, flaps, tail and similar places where bacteria can get a start. Salt helps slow bacterial growth.

As shown on FIG. 6, the dot is the point where the grader touches the screen on the touch screen monitor 25. The grader can move his finger on the screen until the crosshairs on the image 23 on the touch screen monitor 25 are in the proper location at the fifth scute. When the finger from the touch screen monitor 25 is released this marks the beginning of the ruler that is imposed on the screen. The numbers on the ruler are visible on the screen and hide image 23 and show the size of the hide 17.

On the hide image 23 you count back from the first major scale, one, two, three, four, five, then you go to the fifth scute on top and corresponding lower scute to get the measurement.

When you touch the screen on the monitor 25 on the top scute, you get a crosshair displayed on the hide image 23. You then touch the bottom scute on the hide image 23 where you get a crosshair and it measures it, posts it on the screen, and takes a picture. When you look at that picture again and you open it up on a screen you see the grade, measurement, photo of the hide, the barcode number and the RFID number.

The text at the top line of the touch screen monitor 25 reads from left to right as follows.
Scanner ID: RFID: GRADE 1 2 2 4 $5^{th}$ Scute: Nan cm Zoom: 50%
Reset −25% +10% +25% +50%

The text at the second line of the touch screen monitor 25 read from left to right as follows.
Table Id: 347 Operator: Thelma Uploaded Done Enable Speech Ruler Auto Clic ON Clear POI Click Settings The operating system of the computer 27 is Linux. The applications on the computer also run on Linux.

Radio-frequency identification (RFID) is a well-known and utilized technology that uses electromagnetic fields to automatically identify and track tags attached to objects. The tags contain electronically-stored information. Passive tags collect energy from a nearby RFID reader's interrogating radio waves. RFID tags contain an integrated circuit and an antenna, which are used to transmit data to the RFID reader (also called an interrogator). The reader 26 then converts the radio waves to a more usable form of data. RFID tagging is an ID system that uses small radio frequency identification devices for identification and tracking purposes. An RFID tagging system includes the tag itself, a read/write device, and a host system application for data collection, processing, and transmission. Radio Frequency Identification (RFID) is a technology designed to allow objects, animals and even human beings to be identified, located, and tracked using radio frequency signals.

Figure 4:
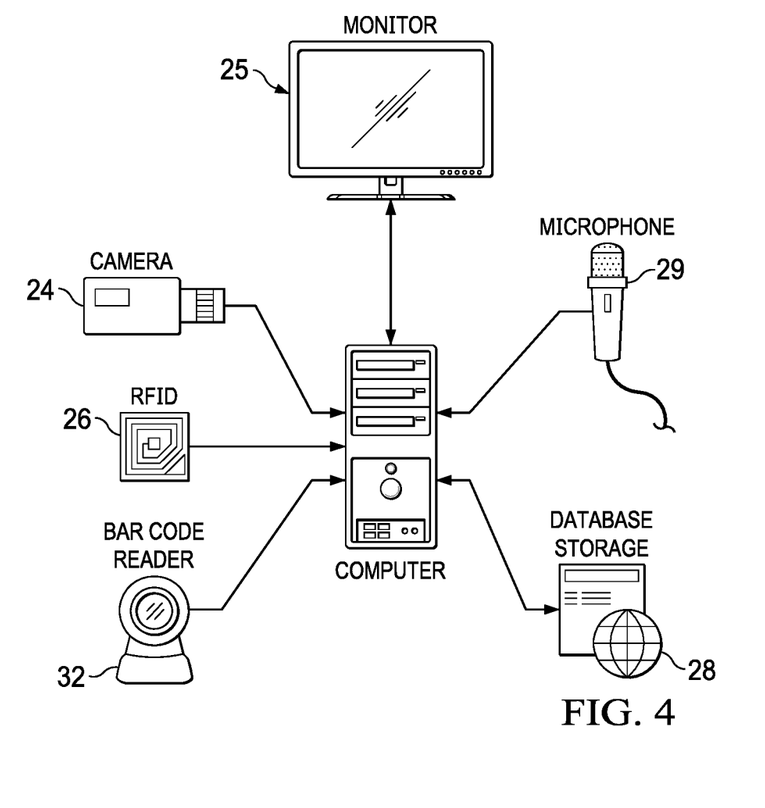
FIG. 4 is a schematic representation of the grading system.

As show in FIG. 4, the monitor 25 and camera 24 and RFID reader 26 and bar code reader 32 are connected to a computer 27. The computer 27 can be connected to the internet and can be connected to a computer LAN. A touch screen monitor 25 is connected to the computer to view the image 23, FIGS. 2-3 and 6 from the camera 24. The camera 24 takes high resolution photos of hides on the light table. The camera 24 may be currently available 4K camera. The touch screen monitor can be used to zoom on to an area of the hide 17 and enlarge the area for viewing. The computer 27 is a standard PC computer with hard drive storage and a connection to the internet. The computer 27 is connected to database storage 28 either by ethernet connection or the internet.

The database storage connected to the computer 27 stores the data it receives from the RFID reader 26, bar code reader 32, touch screen monitor 25 and camera 24. These are used to transmit information to the database storage and send commands to the computer 27.

In operation, a hide 17 is laid on the light table 11 on its translucent top 13 as shown in FIG. 1. The bar reader 32 reads the bar code that is attached to the hide 17 and sends this information to the database storage 28 connected to the computer 27. This bar code information is associated with a profile in the database storage 28 for the computer 27 for each hide 17 and is inserted into the profile in the database storage on the computer 27. Also, a RFID reader 26 can be used to read the RFID chip that is attached to the hide 17 and sends this information to the database storage in the computer 27. This RFID information is associated with a profile in the database storage for the computer 27 for each hide 17 and is inserted into the profile in the database storage on the computer 27.

Additional information regarding each hide 17 can also be stored in the database 28 connected to the computer 27. This may include the coordinates of the origin of the hide 17 and the source of the hide 17 in the United States. Additional information required by the USDA may also be put in the database so that it will be recorded and used in USDA inspections of refrigerated containers for shipping the hides. The hides are tanned and dyed by the customer which may incur in Europe or elsewhere.

The LED light source under the translucent top 12 shines through the semi translucent hide 17 and illuminates the hide 17. The light may also reveal any defects in the hide 17. The grader 20 positions the hide 17 on the translucent top 12 so that it is positioned below the camera 24. The grader 20 can touch the appropriate grade button on the monitor 27 to input the grade into the database 28. The top and lower scutes are identified and the grader 20 touches the monitor 25 at these two points to input their location and get a measurement. The camera 24 takes a high-resolution photograph of the image 23 of the hide 17 which is inserted into the database storage connected to the computer 27. If there is an area of interest on the hide 17 the grader 20 can use the touch screen monitor 25 zoom buttons on the touch screen to zoom in on the area of interest. The camera 24 takes another high-resolution photograph of the area of interest. Even if the screen shows zoomed in, if another picture is taken, it is of the entire camera view NOT the zoomed in area.

The hide 17 may include defects like a hole 21 in the hide 17. The hole 21 in the hide 17 will be illuminated by the light coming through the translucent top 12 and show up on the image 23 on the monitor 25 and be permanently recorded in the photographs. Additionally, if there are no defects in the hide 17 this will also be apparent from the high-resolution photographs of the illuminated hide 17.

During the grading process the Grader 20 assigns a grade to each hide 17 depending on whether it has any defects such as the hole 21. Assuming the hide 17 has no defects, it will be given a Grade 1 which is the default grade. Depending on the quality of the hide 17 it can be given a Grade 1, Grade 2 or Grade 3 by touching the appropriate grade button on the touch screen monitor 25. The grade affects the price of the hide 17.

During the measurement between the top and lower scutes that is set by the grader 20 touching the touch screen monitor 25, a vertical ruler 31 is superimposed on the hide 17 image in the monitor at about its midline and viewable in the monitor 25. The vertical ruler 31 allows the grader 20 to observe and measure the width of the belly of hide 17 which affects its grade. The ruler is calibrated so that it shows accurate measurements on the hide image 23 on touch screen monitor 25.

The top 12 is translucent so the bank of LED lights will shine through it. When you put the hide 17 on the lighted table the hide 17 is a little bit translucent. This allows the grader 20 to see where the little scales part or where there is thinning between the scales. The scales show up as not opaque. You may not see through the scales, but you can see the overall hide 17 through the thinner parts. This allows you to see imperfections. If there are holes in the hide 17 or gaps in it these would show up on the table and photographs of the hide 17. And you now have a record of that and you would know that was there. Then it has the capability to magnify portions of the hide 17. The grader 20 can give commands like Mag 5, Mag 10, Mag 15, Mag 25 and the camera 24 can be zoomed in on a portion of the hide 17 to magnify and verify if there are imperfections.

The components of the system 10 and method are shown in FIG. 4. The camera 24, RFID reader 32, monitor 25, and microphone 29 are all connected to the computer 27. A keyboard and mouse or touchpad may also be connected to the computer 32 and used for setup of the system. During operation, the keyboard and mouse are not used for operation of the system during grading. The touchscreen monitor 25 is used to send commands or data to the computer 32. A cloud or network database 28 is attached to the server to store the database data on each hide 17 that is graded. The cloud or network database 28 can be accessed remotely to allow others to access information in the database.

The steps of process are shown in FIG. 5. After the system 10 is turned on, you can place a hide 17 on the light table for grading. The RFID reader reads the RFID and Wildlife tags on the hide 17 and saves them into the database. A reader can be built into the table so when tag on a hide 17 is on and end of table it is automatically read the ID is stored in the database. A tag on the hide may have to be positioned so the code can be read by a reader 26. A handheld tag reader or scanner could also be used to read ID tags on the hide. The grader 20 views the image of the hide 17 on the light table and the camera 24 takes a picture of the hide 17. The hide 17 is partially translucent so the light makes defects or thin parts visible on the monitor 25. A barcode reader may also be attached to the computer 27 and be used to read tags or labels that have a barcode to identify the hides.

There are various ways that the grader 20 and components can input data into the database. The preferred way is with touch commands on the monitor 25 as described above. The grader 20 can signal the computer 27 to give a grade to the hide by touching the grade button on the screen. The grader 20 then touches the top scute and sets this point and then touches the lower scute and sets this point. This causes the ruler to appear on the image to give a measurement. The camera 24 takes a photo of the hide 17. This can be done with a touch commands on the monitor 25.

The computer 27 may also have a mouse and keyboard for inputting information. The computer 27 may also have a touch pad for inputting information. The keyboard and mouse are only used for setup and are not needed for operation of the grading systems for grading hides. The monitor 25 is a touch screen monitor 25 and can be used to send commands to the computer and camera 24. For instance, the camera 24 could be instructed by touching the monitor 25 or by voice command to zoom in a sector of the hide 17 and magnify it for closer examination. Again, the camera 24 could be instructed on the touch screen to take a photo of the enlarged point of interest on the hide 17 and make a record of it. The grader 20 inputs the grade of the hide 17 by touching the grade button on the screen into the database where it is stored to specify the grade. The grader 20 can use set buttons on the screen to insert user defined notes so that the note does not have to be typed. By setting the crosshairs that give the measurement of the hide this shows up and is displayed on the screen displayed ruler 31 that is superimposed on the image to measure the size of the hide 17. This causes the information put into the database to specify the size. The image on the monitor 25 is then captured automatically after size is set. The image is stored in the database and associated with the other information that is captured and stored in the database.

The system 10 is set up so that it recognizes your touch commands of the grader 20 and can instruct the camera 24 to magnify a sector of the hide 17. The grader 20 can also use the touch commands to cause the camera 24 to take a photograph to make a permanent record. The system 10 makes the grader 20 carefully look at the hide 17 and note the imperfections during the grading process.

The touch screen monitor 25 can also allow the grader 20 to zoom in on a point of interest on a hide 17. The magnified picture can be used to verify if there is an imperfection that affects the grade of the hide 17. A photograph can be made of the point of interest to have a record of it and the reason why the hide 17 was graded.

The procedure of the invention may utilize a person that lays the hide 17 on the light table for grading. A bar code reader 32 and a RFID reader 26 is used to read the bar code and RFID tags. The bar code reader 32 is positioned on the table to read the bar code chip on the identifying bar code label when the hide 17 is laid on the table. The RFID reader 26 may be positioned on the table to read the RFID chip on the identifying tag when the hide 17 is laid on the table. The identification number on the bar code label and the RFID tag are automatically recorded in a database profile for that tag on the hide 17. The bar code reader 32 and RFID reader 26 read the bar code and the RFID tag and the information is stored in the database form in the designated field.

Another problem that is solved is there is not a readily available inventory that is kept for years. The hide 17 that is being graded came from a latitude and longitude for where it came from. A person that buys a purse for $50,000.00 may want to know the history of the alligator hide 17. People may want to know the history and how much you paid for them.

This gives the seller the ability to have a readily accessible inventory where people can locate where the hide 17 originated from which may solve a problem of marketability. This allows the buyer and seller to keep track of where the hide 17 came from and what it looked like at the time it was graded. By pulling the photo of the hide 17 up on a monitor 25 you can answer any question. The buyer may try to downgrade the hide grade because it saves them money even though it costs the person selling the hides. The seller can use the grading system to verify whether the grade the seller's grader gave is correct. This can be done without having someone present at the seller's location to make the evaluation of a hide.

The hides are shipped in a refrigerated case or container with as many as 500 hides with a manifest of radio frequency identification numbers and listed on a manifest with RFDI Nos. and Grade Nos. There is a manifest and which is a list identifying them by RFDI.

The USDA may then break open the case and pull out hides to inspect them. The hides must be re-wrapped and placed back in the refrigerated case. They are refrigerated so they will not spoil since they are not tanned yet. The process is that the hides are removed from the animal carcass and salted. After they hide them, they salt them, they grade them, then they wrap them and put them in the container for shipping. A list of the hides is included with the bar code number and any RFDI number and the Grade number. The hides are shipped in the refrigerated case to preserve them because they haven't been tanned yet.

The USDA inspector inspects the hides and makes sure they come from a licensed source of hides. The USDA checks for the bar code and any RFDI tags to identify the hide. Since it contains alligator hides, the USDA wants to make sure the hides have a label and tag on them. If a hide does not have a label and tag it may be confiscated, and the seller fined. The inspection of the hides occurs at the export dock by the United States Department of Agriculture's division called Wildlife and Fisheries.

You can use that system 10 for the USDA inspectors. You can create a report from the database and load it on a USB drive or print out a copy. You may also email photos and a report and give the USDA inspector a printout. Or the USDA inspectors can display it on a monitor 25. Using this system 10 they may not have to open the refrigerated case to see every hide in there and can do a better inspection than if they pulled the hides out and inspected a few of the hides.

The hides are raised on a farm and they are not caught in the wild. Eggs are taken from the wild alligators. The alligators that are skinned are raised on farms. The alligator meat is sold as a by-product. They are tanned and dyed by the customer.

For every skin that is harvested the USDA makes sure the alligators are repopulated. If 100,000 alligator eggs are harvested from the wild, you must give 12 percent back to the wild. During grading of the live alligators, they put the smaller ones back to grow large to maintain the population. You must keep track of every one of the number of eggs you harvest from the wild. There is a LAT log giving the latitude and longitude of where each alligator comes from. It is the GPS location. Customers want to know where the alligator was raised and where the hide comes from and who raised it. You may email photos to a customer to verify the inspection grade. The buyer and seller can compare the hide with the photos and verify the inspection grade.

The alligator is an endangered species, so they keep track of every alligator that is harvested. One problem with this is that there can be human error in grading and bad data entry.

After the alligator is harvested the skin is given a bar code No. label and may get an RFDI No. tag that is clamped onto the hide. When it comes from people who harvest the gator the buyer puts a government tag on it. And when it gets to the tannery, for their own records the buyer also puts another tag on it. The USDA mandates that you put a USDA approved label or tag on the hide. When the animal hide leaves the docks of Louisiana and gets to the port of entry overseas for tanning with the USDA government label tag the buyer puts a new tag on. You now have two tags on the skin, the government tag and the new buyer tag.

The USDA inspects the hides in a refrigerated container before they are shipped to Europe. This may require opening of the container and removal of the hides. An object to the invention is to allow the USDA to inspect the hides.

When the hides arrive at the buyer's place of business, the buyer has an inspector that views each hide and verifies that it was given the correct grade. If the inspector downgrades the hide grade the seller can then view the photographs taken during the seller's grading and verify if the buyer grader 20 is correct in downgrading the hide grade.

The seller saves money by using the system 10 because it makes it more difficult for the buyer to down grade a hide and reduce the price. The Grade 1 hide brings the most money and the price goes down as the Grade goes down. Some high-end buyers will only take a Grade 1 hide.

With the system 10 and method of the invention an online auction is possible since multiple buyers could bid on the same hides. The invention gives a seller peace of mind and is useful for evaluation and training graders. It makes possible a manifest on a USB flash drive with the images. The grading process takes less time and fewer personnel. It helps reduce grading errors. The USDA benefits from the system 10 with the manifest and images that it can utilize on a USB drive or by accessing the images on the database. The person grading no longer needs a ruler, the system 10 is ergonomic, touch screen input allows the grader 20 to merely touch the touch screen monitor 25 to input the information. The grader 20 and use the touch screen monitor 25 to zoom in on a point of interest. The grid overlay can be calibrated to accurately show the size of the hide without having to lay a ruler on the hide and make the measurements. The seller has an easy to access inventor that is matched to the government ID tag and stored in the cloud.

If a buyer challenges the grade given to hides the seller can pull up the images of the hide and discuss them with the buyer who can view the hide or display the image. This allows the buyer to challenge a grade reduction of a hide by the buyer and resolve this without having to travel to the seller's location to see the reason for the downgrade.

The above-listed sections and included information are not exhaustive and are only exemplary of the invention. The sections and included information in an embodiment may depend upon the implementation and the included devices and resources. Although a system 10 and method according to the present invention have been described relating to the preferred embodiment, it is not intended to be limited to the specific form set forth herein, but, on the contrary, it is intended to cover such alternatives, modifications, and equivalents, as can be reasonably included within the spirit and scope of the invention as defined by the appended claims.

The above-listed sections and included information are not exhaustive and are only exemplary of the invention. The sections and included information in an embodiment may depend upon the implementation and the included devices and resources. Although a system and method according to the present invention have been described relating to the preferred embodiment, it is not intended to be limited to the specific form set forth herein, but, on the contrary, it is intended to cover such alternatives, modifications, and equivalents, as can be reasonably included within the spirit and scope of the invention as defined by the appended claims.

We claim:

1. A method for grading and verifying the grading of an animal hide comprising the steps of:
    Inspecting an animal hide on a light table to allow determination of the grade of the hide;
    Reading a tag or label on the hide to identify the hide;
    Displaying the hide on a touch screen monitor connected to a computer;
    Selecting the grade of the hide on a touch screen monitor;
    Selecting the top and lower scutes on the monitor image of the hide with touch commands on a touch screen monitor to provide a measurement of the hide between scutes; displaying a ruler on the animal hide image so that its dimensions are shown on the image;
    Photographing the animal hide on the light table with a camera;
    Storing the photograph of an animal hide and all information relating to the animal hide in a database to identify the hide and to provide verification of the inspection grade of the animal hide.

2. The method of claim 1, including the step of:
    The location of the top and lower scutes is set by touching the monitor at one location and then at another location which gives a measurement of the distance between the scutes.

3. The method of claim 1, including the step of:
    Reading a bar code on the hide with a bar code reader that associates the bar code with the information collected on the hide.

4. The method of claim 1, including the step of:
    Reading an RFID tag on the hide with an RFID reader that associates the RFID information with the information collected on the hide.

5. The method of claim 1, including the step of:
    Displaying the database storage information for a hide at a remote location of verify the information on the hide.

6. The method of claim 1, including the step of:
    Using touch commands on the touch screen monitor to zoom the camera in on the hide to display points of interest.

7. The method of claim 1, including the step of:
    Storing the information in a cloud-based database.

8. The method of claim 1, including the step of:
    inputting information into the database storage with voice recognition software.

9. A system for grading and verifying the grading of an animal hide comprising:
    a light table for inspecting an animal hide to determine the grade of the hide;
    a tag or label reader for identifying the hide;
    a camera connected to a computer for displaying the hide on a monitor connected to a computer and for photographing the animal hide on the light table with the camera and storing the data and image in a computer database storage to make a record of the inspection and provide the ability to verify the condition of the animal hide when it was inspected;
    a ruler for displaying on the animal hide on the monitor so that the hide dimensions can be observed and can be recorded on in a database storage;

a touch screen monitor for inputting information into a database storage to make a record of the inspection and grading of the hide, a database storage for storing the photograph of an animal hide and all information relating to the animal hide to identify the hide and to verify the grade given to an animal hide.

10. The system of claim 9, comprising;
The camera has a zoom mode that allows it to zoom in on a point of interest on the hide for a photograph.

11. The system of claim 9, comprising;
The database storage is a cloud-based storage.

12. The system of claim 9, comprising;
The ruler is a vertical ruler.

13. The system of claim 9, comprising;
The device for inputting information into a database storage to make a record of the inspection and grading of the hide touch screen input buttons for inputting information into the database storage.

14. The system of claim 9, comprising:
The database storage information is connected to the internet for displaying information for a hide at a remote location to display the identity, grade or authenticity of the hide.

15. The system of claim 9, comprising:
The tag or label reader is a bar code reader for reading information on bar code labels on the hide.

16. The system of claim 9, comprising:
The tag or label reader is an RFID reader for reading information on RFID tags for the hide.

17. The system of claim 9, comprising:
Voice recognition software for inputting information into the database storage.

* * * * *